United States Patent [19]

Settepani

[11] 4,004,017
[45] Jan. 18, 1977

[54] METHOD OF INDUCING INFERTILITY IN MALE ANIMALS AND INHIBITING THE GROWTH OF THE PROSTATE

[75] Inventor: Joseph A. Settepani, Somerville, N.J.

[73] Assignee: Ortho Pharmaceutical Corporation, Raritan, N.J.

[22] Filed: July 31, 1975

[21] Appl. No.: 600,663

Related U.S. Application Data

[60] Division of Ser. No. 381,963, July 23, 1973, Pat. No. 3,932,651, which is a continuation-in-part of Ser. No. 137,426, April 26, 1971, abandoned.

[52] U.S. Cl. .............................. 424/274; 424/248.5; 424/250; 424/267; 424/322; 424/327

[51] Int. Cl.² ............... A61K 31/495; A61K 31/15; A61K 31/40; A61K 31/445

[58] Field of Search ................................... 424/274

Primary Examiner—Stanley J. Friedman
Attorney, Agent, or Firm—Benjamin F. Lambert

[57] ABSTRACT

3,5-bis(substituted amino)-1,2,4-dithiazolium salts, 3-substituted amino-5-substituted imino-1,2-4-dithiazolidine salts and dithiobiuret intermediates are administered to male animals to inhibit fertility and to inhibit the growth of, or reduce the size of, the prostate gland and the seminal vesicle.

3 Claims, 2 Drawing Figures

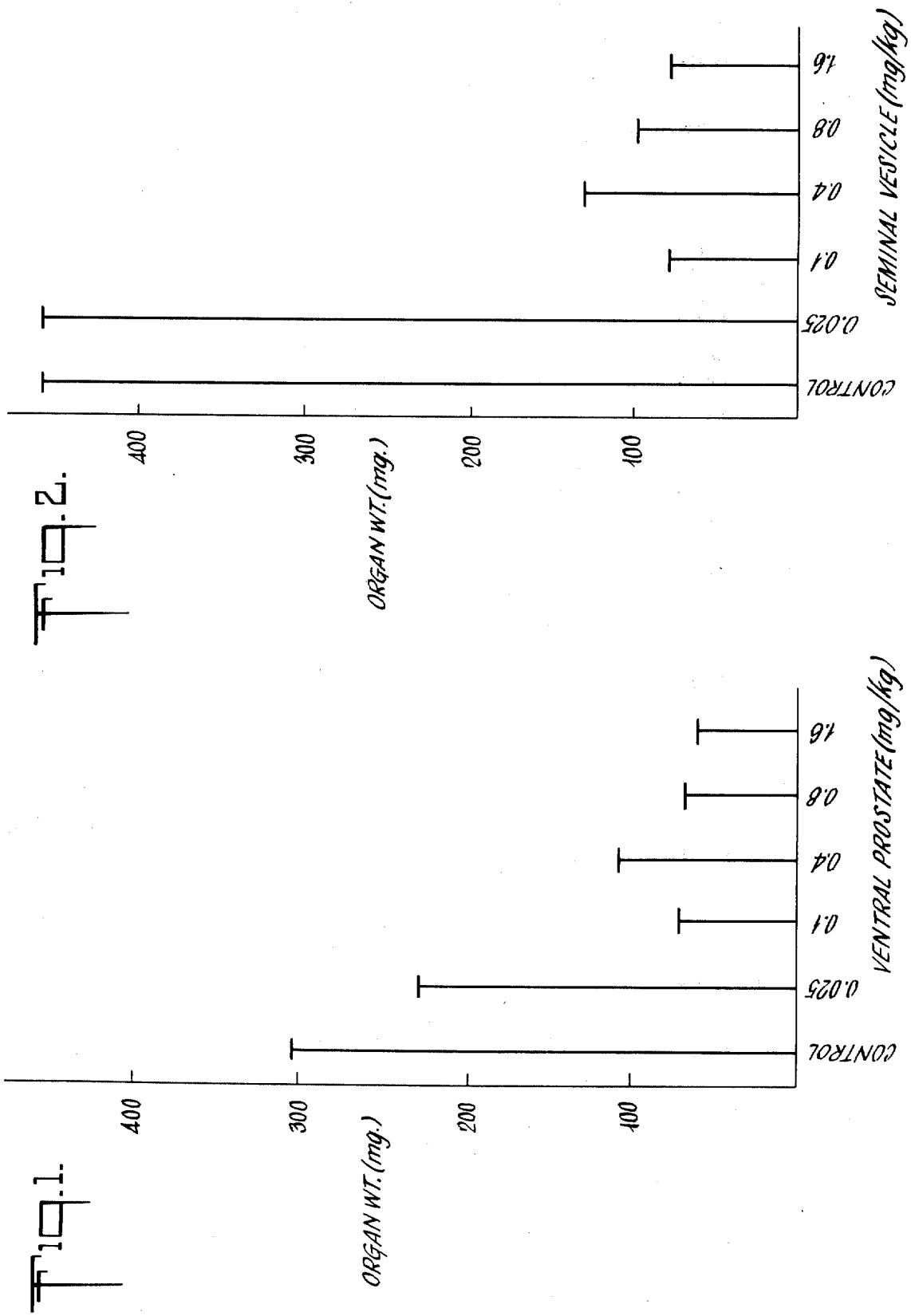

METHOD OF INDUCING INFERTILITY IN MALE ANIMALS AND INHIBITING THE GROWTH OF THE PROSTATE

This is a division of application Ser. No. 381,963 filed July 23, 1973, now U.S. Pat. No. 3,932,651, which is a C-I-P of Ser. No. 137,426, filed Apr. 26, 1971, now abandoned.

The possibility of chemically inducing infertility in male animals has intrigued investigators for a number of years and many have worked toward the discovery of an antispermatogenetic agent. Such a compound would, by definition, interfere with one or more phases of the complex series of cellular events which constitute the process of spermatogenesis. While some such compounds have been found which are active in man, clinical usefulness of these compounds is limited by the delay in the onset of sterility, the delay in the return of fertility once medication is terminated, and a narrow margin of safety.

One approach to the problem has been to attempt to synthesize potent, non-hormonal antigonadotrophic agents having a localized effect on the germinal epithelium to induce sterility as a consequence of androgen deprivation. Such compounds would also cause marked atrophy of the Leydig cells, the prostate gland, and the seminal vesicles. Depopulation of spermatids from the seminiferous epithelium would also be a normal consequence of the androgen deprivation.

It has now been discovered that 3,5-bis(substituted amino)-1,2,4-dithiazolium salts and 3-substituted amino-5-substituted imino-1,2,4-dithiazolidine salts are potent antigonadotrophic agents when administered in effective non-toxic doses to male animals.

The compounds which are the subject of the method of the present invention fall within the general formula:

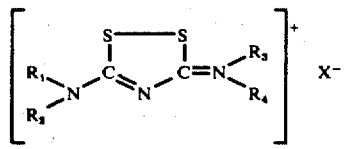

wherein X represents an anion of an acid having an ionization constant of at least $1 \times 10^{-7}$, $R_1$, $R_2$ and $R_3$ are selected from alkyl having 1 to 36 carbon atoms such as, for example, methyl, ethyl, dodecyl, cyclohexyl, methylstearyl, stearyl and the like; aryl having 6 to 10 carbon atoms such as, for example, phenyl, tolyl, tolylphenyl, napthyl, and the like; alkyl aryl having 7 to 12 carbon atoms such as, for example, methylphenyl, butyltolyl, cyclohexylphenyl and the like; $R_4$ is hydrogen, alkyl having 1 to 36 carbon atoms, aryl having 6 to 10 carbon atoms, and alkyl aryl having 7 to 12 carbon atoms, and

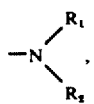

and

may be hydrazono or a heterocyclic group such as a piperidino, morpholino, pyrrolidino, piperazino or a hydrazono group.

The acids which form stable salts with the compounds employed in the method of the present invention may be organic or inorganic acids. Suitable acids are those which have an ionization constant of at least $1 \times 10^{-7}$ and preferably at least $1 \times 10^{-6}$ and include hydrochloric acid, hydrobromic acid, hydrofluoric acid, hydriodic acid, sulfuric acid, nitric acid, thiocyanic acid, phosphoric acid, sulfurous acid, fatty acids, particularly acetic acids, chlorinated fatty acids, particularly mono-, di-, and trichloroacetic acids, oxalic acid, tartaric acid, dinitrophenol, trinitrophenols, particularly picric acid, benzoic acid, toluic acid and napthoic acid.

Preferred among the above compounds are those compounds wherein $R_1$, $R_2$, $R_3$ and $R_4$ are alkyl, morpholino and piperidino and X is chloro or nitro.

It has also been found that the dithiobiuret compounds, which are isolatable intermediates in the preparation of the dithiazolium compounds, are also active antigonadotrophic agents. It is hypothesized that either these compounds undergo cyclization to active dithiazolium salts in vivo or the dithiazolium salts undergo degradation in vivo to the corresponding dithiobiuret compound. The active dithiobiuret compounds are represented by the formula:

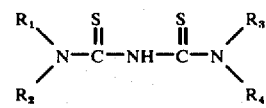

wherein $R_1$, $R_2$, $R_3$ and $R_4$ are as defined above.

The compounds utilized in the method of this invention are, for the most part, disclosed and claimed in U.S. Pat. No. 3,166,564 which issued to Diveley. These compounds are disclosed in the Diveley patent as being useful as defoliants. The compounds used in the method of this invention are thus prepared in the manner described in U.S. Pat. No. 3,166,564. The general procedure for the preparation of the compounds is illustrated below.

PREPARATION A 3,5-bis(dimethylamino)-1,2,4-dithiazolium chloride

A vessel provided with a cooling jacket, thermometer, condenser, and inlet tube is charged with 2300 parts of acetone and 270 parts of potassium thiocyanate and stirred until homogeneous. Then 334 parts of dimethyl thiocarbamylchloride is added and the mixture stirred and heated at about 55° C. for 10 minutes. The mixture becomes yellow and potassium chloride separates out of solution. The mixture is cooled and filtered (suction), and the salt cake is washed with acetone. The filtrate (including washings) is charged back into the same vessel. Then 121.5 parts of dimethylamine is passed in at a rate of 1 to 1.5 parts per minute with stirring and cooling to keep the temperature below 30° C. After stirring for an additional half hour, the mixture is aspirated for 5 minutes to remove excess amine. Following removal of the amine, 173 parts of chlorine are introduced into the solution at a rate of 1 to 2 parts per minute while stirring and cooling to keep the temperature below 30° C. The mixture becomes orange-colored and a solid begins to separate almost immediately. The mixture then becomes yellow as the reaction progresses and the solid becomes voluminous. After the chlorine addition is complete, the solid product is filtered (suction), washed with acetone twice and dried in the air overnight. The dried product amounts to 500 parts of 3,5-bis(dimethylamino)-1,2,4-dithiazolium chloride, representing a conversion of about 82% based on the acid chloride and a yield of about 92% based on the chlorine used, in the average run. The products are usually light tan or very light yellow in color. The product is further purified by making a concentrated aqueous solution (½ part water, 1 part product), warming slightly, filtering, and re-precipitating the product from the filtrate with acetone. The purified product is white and melts at 267°–270° C. (dec.).

The dithiazolidine and the hydrazono compounds are prepared in the same manner as the dithiazolium compounds by using a primary amine and a substituted hydrazine respectively in place of the secondary amine.

An example of the utility of the above-noted compounds may be illustrated by mating studies carried out with 3,5-bis(dimethyl amino)-1,2,4-dithiazolium chloride. In testing the compounds, an experimental group of male animals such as rats, rabbits, or mice, for example, are fed a basic diet containing the compound to be tested. For the purpose of illustration, adult male rats will be employed as the test animal.

EXAMPLE 1

Adult male rats of a Wistar derived strain are housed five to a cage in air-conditioned animal quarters and maintained on laboratory chow and tap water ad libitum. The compound is dissolved in propylene glycol and administered once daily intragastrically for 14 consecutive days. An equal number of controls receive only the propylene glycol. At the end of the treatment, each male is cohabited with a proestrus female. Each morning the vaginal washings are taken and examined for the presence of sperm. The males are sacrificed and the reproductive organs examined. Nine days post-mating, the females are autopsied and examined for implantations. Males failing to mate, judged by the absence of sperm in vaginal washings, are re-cohabited with proestrus females until mating does occur. While a reduction in libido as well as fertility is noted at high doses, the antifertility effects even at those doses cannot be attributed wholly to the loss of libido since sperm are found in the vaginal smear of the mated females in which pregnancy does not develop.

A careful examination of the organs of the sacrificed male rats indicates that treatment with as little as 0.1 mgs. per kg. (approximately 25 micrograms per rat per day) of the compound cause marked atrophy of the Leydig cells, the prostate gland, and the seminal vesicles. Depopulation of spermatids from the seminiferous epithelium is also observed. At this dosage level, loss of libido is not significant. Of the four male rats successfully mated, two mates are found to be pregnant, thus indicating that there is also local action on the spermatozoids resident in the epididymis. It is also found that when the above-noted compound and testosterone propionate are simultaneously administered, there is a neutralized response on the male accessory organs thus indicating that the effect of the compound is not due to the peripheral antagonism to testicular steroid hormones. Thus, it is hypothesized that interference with the action of pituitary gonadotrophin or the formation or secretion of gonadotrophin is the way in which this compound asserts its effects. The local effect on the spermatozoids resident in the epididymis is more pronounced at slightly higher doses as is illustrated by the fact that upon treatment with 0.5 mgs. per kg., of the rats successfully mated, none of the females is found to be pregnant at this dosage level. The effect on libido is still minor.

Because of the potency of the compounds involved, the amount of a given compound to be employed will depend upon the particular species being treated. It has been found, for example, that doses of greater than 1.0 mg. per kg. per day in the rat should be avoided.

The specific dose and regimen utilized will depend on the species and the specific compound chosen. An effective dose for a particular species and compound can be readily determined by routine clinical and laboratory screen.

The effect of the administration of the compounds of this invention on the prostate and the seminal vesicle can be seen in FIG. 1 and FIG. 2 which illustrate the size of those organs of the rats treated as described above.

Using the procedure illustrated in Example 1 above, the following results were obtained:

| EX | COMPOUND | DOSAGE |
|---|---|---|
| 2 | 3-dimethylamino-5-morpholino-1,2,4-dithiazolium chloride | 20 mg/kg - 4/5 of males mated. None of females had implanted embryos. |
| 3 | 3-dimethylamino-5-methylimino-1,2,4-dithiazolidine hydrochloride | 10 mg/kg - 3/5 of males mated. 0/3 females had implanted embryos. |
| 4 | 3-dimethylamino-5-piperidino-imino dithiazolidine hydrochloride | 10 mg/kg - 5/5 mated; 1/5 females had implanted embryos. |
| 5 | 3-morpholino-5-isopropylimino-1,2,4-dithiazolidine hydrochloride | 20 mg/kg - 4/5 of males mated, 0/4 females had implanted embryos. |

What is claimed is:

1. A method of inhibiting fertility in male animals and of reducing the size of the prostate and the seminal vesicle in male animals which comprises orally administering to a male animal an effective non-toxic amount of a compound of the formula:

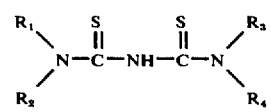

wherein $R_1$, $R_2$, and $R_3$ are alkyl having 1 to 36 carbon atoms, aryl having 6 to 10 carbon atoms, or alkyl aryl having 7 to 12 carbon atoms, $R_4$ is hydrogen, alkyl having 1 to 36 carbon atoms, aryl or alkyl aryl; and
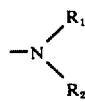
and
are each pyrrolidino.
2. The method of claim 1 wherein $R_1$, $R_2$, $R_3$ and $R_4$ are alkyl.
3. The method of claim 2 wherein $R_1$, $R_2$, $R_3$ and $R_4$ are methyl.
* * * * *